United States Patent
White et al.

(10) Patent No.: US 11,345,944 B2
(45) Date of Patent: May 31, 2022

(54) METHODS AND SYSTEMS FOR RAPID CONTINUOUS FLOW PATHOGEN CELL LYSIS IN A MICROFLUIDIC CHANNEL

(71) Applicants: Canon U.S. Life Sciences, Inc., Rockville, MD (US); UNIVERSITY OF MARYLAND, College Park, MD (US)

(72) Inventors: Ian M. White, Ellicott City, MD (US); Stephen Restaino, Columbia, MD (US); Marina Pranda, Rockville, MD (US)

(73) Assignees: Canon U.S.A., Inc., Melville, NY (US); University of Maryland, College Park, MD (US)

( * ) Notice: Subject to any disclaimer, the term of this patent is extended or adjusted under 35 U.S.C. 154(b) by 0 days.

(21) Appl. No.: 14/586,499

(22) Filed: Dec. 30, 2014

(65) Prior Publication Data
US 2015/0184218 A1 Jul. 2, 2015

Related U.S. Application Data

(60) Provisional application No. 61/922,509, filed on Dec. 31, 2013.

(51) Int. Cl.
| | | |
|---|---|---|
| *C12Q 1/24* | (2006.01) | |
| *C12M 3/06* | (2006.01) | |
| *C12Q 1/34* | (2006.01) | |
| *C12M 3/00* | (2006.01) | |
| *C12Q 1/37* | (2006.01) | |

(52) U.S. Cl.
CPC ............... *C12Q 1/24* (2013.01); *C12M 3/00* (2013.01); *C12M 23/16* (2013.01); *C12Q 1/34* (2013.01); *C12Q 1/37* (2013.01)

(58) Field of Classification Search
CPC ...... C12Q 1/24; C12Q 2565/629; C12Q 1/34; C12Q 1/37; C12M 3/00; C12M 23/16
See application file for complete search history.

(56) References Cited

U.S. PATENT DOCUMENTS

| | | | |
|---|---|---|---|
| 7,211,320 B1* | 5/2007 | Cooper | A61L 2/0082 210/263 |
| 2005/0269257 A1 | 12/2005 | Voute et al. | |
| 2007/0015179 A1* | 1/2007 | Klapperich | B01J 20/28042 435/6.14 |
| 2010/0203521 A1* | 8/2010 | Klapperich | C01B 32/15 435/6.13 |
| 2010/0224255 A1* | 9/2010 | Mathies | B01F 5/10 137/1 |
| 2011/0294205 A1* | 12/2011 | Hukari | C12Q 1/6806 435/325 |

OTHER PUBLICATIONS

Hanora et al. "Capture of bacterial endotoxins using a supermacroporous monolithic matrix with immobilized polyethylenenimine, lysozyme or polymyxin B" Journal of Biotechnologyvol. 118, Issue 4, Sep. 10, 2005, pp. 421-433.*
Byun et al. "Pumps for microfluidic cell culture" Electrophoresis 2014, 35, 245-257.*
1. Grover "Microfluidic Molecular Processors for Computation and Analysis" Graduate Division of the University of California, Berkeley, Spring 2006, pp. 1-231.*
Mahalanabis et al., "Cell lysis and DNA extraction of gram-positive and gram-negative bacteria from whole blood in a disposable microfluidic chip," Lab Chip, 9, 2811-2817 (2009).

* cited by examiner

*Primary Examiner* — Blaine Lankford
(74) *Attorney, Agent, or Firm* — Rothwell, Figg, Ernst & Manbeck, P.C.

(57) ABSTRACT

The present invention relates to methods and systems for cell lysis in a microfluidic device. More specifically, embodiments of the present invention relate to methods and systems for rapid continuous flow pathogen cell lysis. In one embodiment, the microfluidic device comprises a microfluidic channel, a microporous structure within the channel, and an enzyme immobilized on the surface of the microporous structure configured to lyse pathogen cells in fluid flowing through the microfluidic channel.

10 Claims, 5 Drawing Sheets

METHODS AND SYSTEMS FOR RAPID CONTINUOUS FLOW PATHOGEN CELL LYSIS IN A MICROFLUIDIC CHANNEL

CROSS-REFERENCE TO RELATED APPLICATIONS

This application claims the benefit of U.S. Provisional Patent Application Ser. No. 61/922,509, filed on Dec. 31, 2013, which is incorporated herein by reference in its entirety.

BACKGROUND

Field of the Invention

The present invention relates to methods and systems for cell lysis. More specifically, embodiments of the present invention relate to methods and systems for rapid continuous flow pathogen cell lysis on a microfluidic device.

Discussion of the Background

Cell lysis has many different applications. In particular, the rapid processing of whole blood is useful for the diagnosis of bloodstream infections. While healthcare providers wait on current methods to process whole blood and diagnose a specific infection, it is necessary to use broad-range therapies to treat infected patients, resulting in higher healthcare costs and increasing antibiotic resistance of pathogenic bacteria. Similarly, healthcare providers may have a desire to process other types of biological samples to diagnose infections, including, but not limited to, sputum, urine, cerebrospinal fluid, and the like.

Conventional cell lysis, in which the lipid membrane and cell wall are disrupted chemically, cannot work for the purposes of rapidly processing pathogenic cells. In conventional chemical cell lysis, cells must be lysed in lysis buffer and complete cellular lysis may require incubation for a prolonged period of time as well as agitation of the sample by vortexing or shaking Cell lysis in the context of microfluidic devices is also problematic. If the enzyme and sample are simply mixed while flowing through a microfluidic channel the microfluidic device, there is not enough residence time in the channel for cell lysis to be effective. Further, the lysis buffer may interfere with downstream processing. Mechanical lysis using rigid microstructures has been used for continuous flow lysis of mammalian cells, but is extremely challenging for pathogen cells because of the small size of the pathogen cells.

Chemical and mechanical methods have been used to attempt rapid pathogen cell lysis. For instance, Mahalanabis et al. (Lab Chip, 2009, 9, 2811-2817) reported a microfluidic system involving a hybrid chemical/mechanical method for lysing pathogen cells. They reportedly achieved a 13.3-16.6 µL/min flow rate, and their process reportedly involved two 30-90 minute enzyme incubations and a combination of detergents.

There are several problems with the current technology of pathogen cell lysis. First, the conventional approach is slow. Usually, the conventional approach takes hours or days to finish. This is partly because the conventional approach requires multiple enzyme incubations and requires cells to sit in a lysis buffer. The conventional approach does not utilize a rapid, continuous flow. That is, cells must sit in the lysis buffer in order for the enzymatic reaction to be effective. Another problem is that such methods rely on detergents or chaotropic salts, which are also slow and can inhibit downstream PCR. The presence of these lysis buffer components can also necessitate additional steps to separate them from the DNA to be used in later applications.

Although various methods and devices exist to lyse pathogen cells, none of these provides or describes a single device that is capable of rapid continuous flow cell lysis of pathogen cells. Thus, there is a need to develop improved microfluidic systems and methods for rapid continuous flow cell lysis.

SUMMARY OF THE INVENTION

The present invention relates to methods and systems for rapid continuous flow cell lysis. More specifically, embodiments of the present invention relate to methods and systems for the isolation of pathogen cells on a microfluidic device.

In one aspect, the present invention provides a microfluidic device for rapid continuous flow pathogen cell lysis. In one embodiment, the microfluidic device comprises a microfluidic channel and a microporous structure located within the microfluidic channel. The microfluidic device further comprises an enzyme immobilized on a surface of the microporous structure which is configured to lyse pathogen cells in fluid flowing through the microfluidic channel.

In some embodiments, the microporous structure is a monolith, which could be, for example, a polymer monolith or a silica monolith. In other embodiments, the microporous structure is a packed column of beads. In one embodiment, the beads have bifunctional chemistry. In some embodiments, the beads are made from material having bifunctional chemistry. In other-embodiments, the beads are coated with a material having bifunctional chemistry. One example of a material having bifunctional chemistry is chitosan. Other examples are well known to the skilled artisan. In additional embodiments, the enzyme comprises one or more proteolytic enzymes, for example, lysozyme and/or proteinase K. In some embodiments, the enzyme is covalently immobilized on the surface of the microporous structure. In some embodiments, the pathogen cells are bacterial cells (which can include gram-positive and gram-negative bacteria). In other embodiments, the pathogen cells are other types of pathogens, such as, for example, fungal cells. In some embodiments, the enzyme is configured to lyse pathogen cells in fluid flowing through the microporous structure in the microfluidic channel to provide a sufficient residence time in the microporous structure to lyse the pathogen cells.

In another aspect, the present invention provides a method for rapid continuous flow pathogen cell lysis. In one embodiment, the method comprises introducing pathogen cells into a microfluidic channel of a microfluidic device, wherein the microfluidic channel comprises a microporous structure with a lysis-promoting enzyme immobilized on a surface of the microporous structure. The method further comprises flowing the pathogen cells through the microporous channel of the microfluidic device, whereby the pathogen cells are lysed by the enzymes immobilized on the microporous structure. In some embodiments, the microporous structure is a monolith, which could be, for example, a polymer monolith or a silica monolith. In other embodiments, the microporous structure is a packed column of beads, as described herein. In some embodiments, the pathogen cells are bacterial cells. In additional embodiments, flowing the pathogen cells through the microfluidic channel comprises flowing the pathogen cells at a flow rate to provide sufficient residence time in the microporous structure to lyse the pathogen cells. In some embodiments a flow rate of at least about 20 to about 2000 µL/min, or at least about 20 to about 1000 µL/min, or at least about 50 to 500 µL/min, or at least about 50 to about 200 µL/min, or at least about 100 µL/min is utilized.

In some embodiments, the method further comprises providing the microfluidic device, wherein said microfluidic device comprises a microporous structure located in a microfluidic channel, and immobilizing a lysis-promoting enzyme on the surface of the microporous structure within the microfluidic device, before introducing pathogen cells into the microfluidic channel.

In another aspect, the present invention provides a method for making a microfluidic device. In one embodiment, the method comprises providing a microfluidic device, wherein said microfluidic device comprises a microporous structure located in a microfluidic channel. The method further comprises immobilizing a lysis-promoting enzyme on the surface of the microporous structure within the microfluidic channel of the microfluidic device.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF PREFERRED EMBODIMENTS

Figure 1:
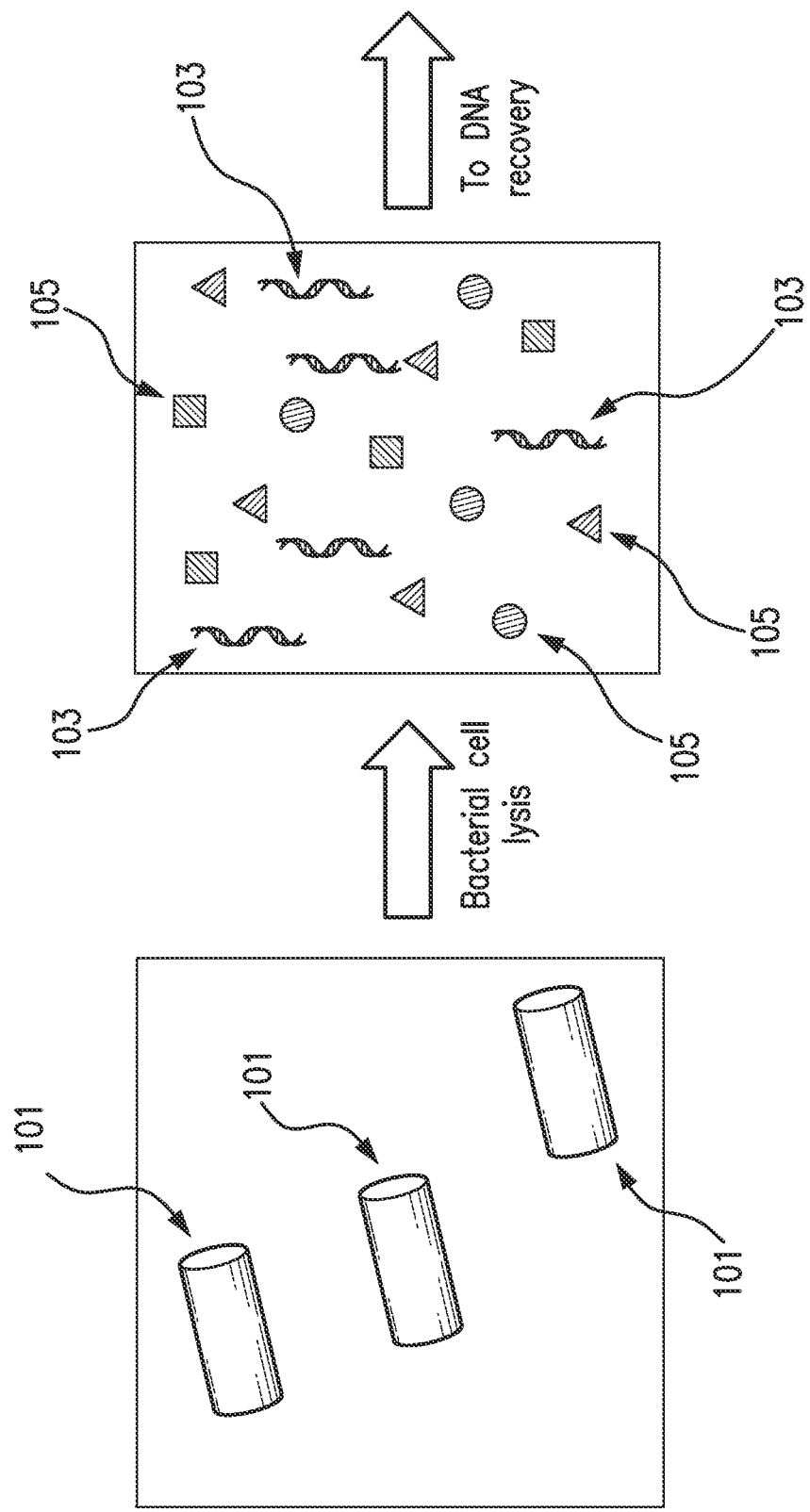
FIG. 1 shows a schematic illustration of pathogen cell lysis.

FIG. 1 shows a schematic illustration of pathogen cell lysis. As illustrated in FIG. 1, when pathogen cells 101 (e.g. bacterial or fungal cells) are lysed, the cell wall or membrane is disrupted, resulting in DNA 103 and other fragments of the cell 105 being released. When cell lysis occurs in a microfluidic device, the DNA 103 can be separated from the other fragments 105 and recovered in a downstream process.

Figure 2:
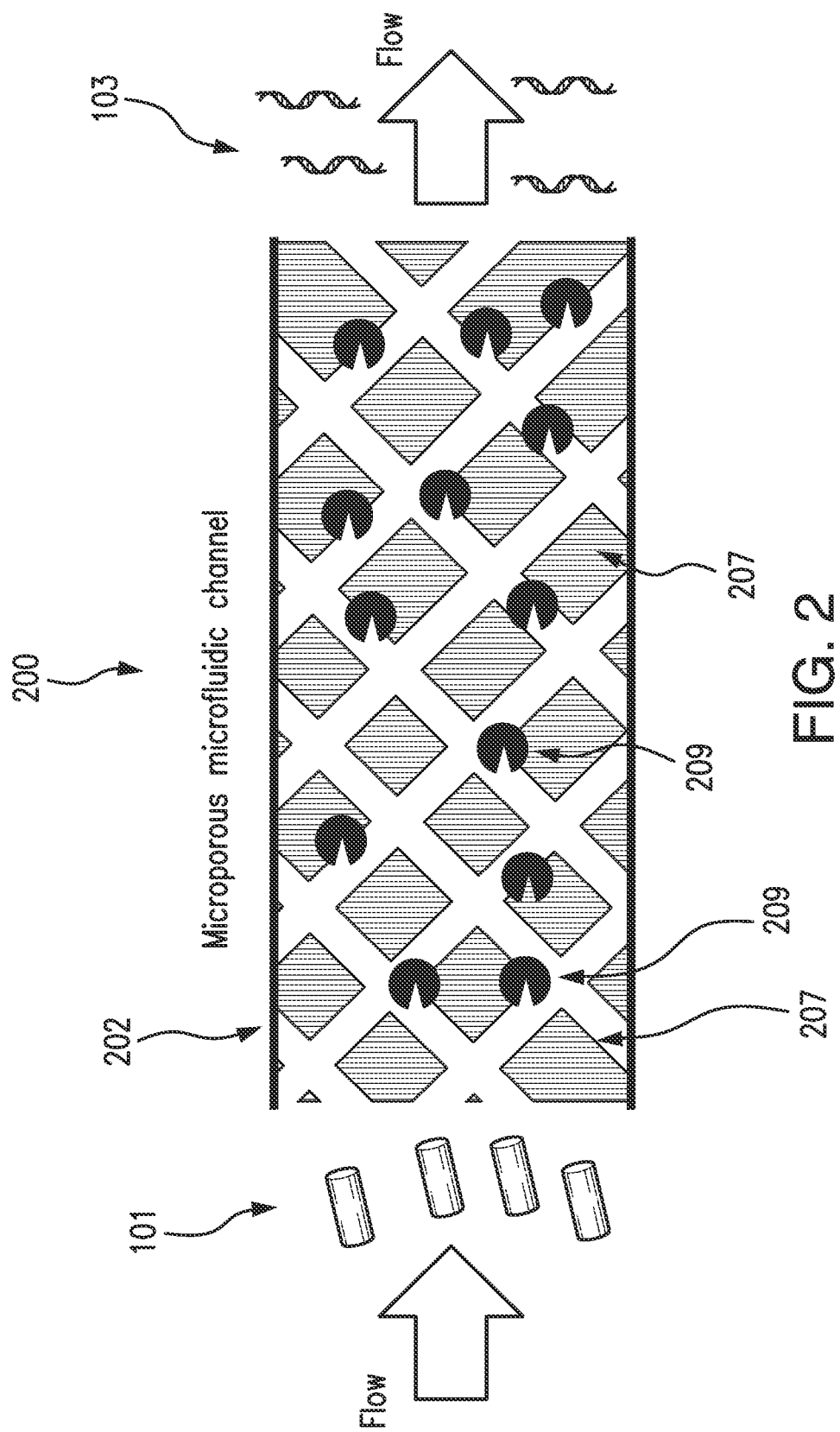
FIG. 2 shows a schematic illustration of a microfluidic device having a microporous monolith structure in accordance with an embodiment of the invention.

FIG. 2 shows a schematic illustration of a microfluidic device 200 having a microporous monolith structure 207 in accordance with an embodiment of the invention. As illustrated in FIG. 2, microfluidic device 200 comprises a microfluidic channel 202 and a microporous structure 207 located within the microfluidic channel 202. The microporous structure IP 207 may be, for example, a monolith made of, for example, polymer or silica. Microfluidic device 200 further comprises an enzyme 209 immobilized on the surface of the microporous structure 207. The immobilized enzyme 209 is configured to lyse pathogen cells in fluid flowing through the microfluidic channel 202 and microporous structure 207.

Figure 3:
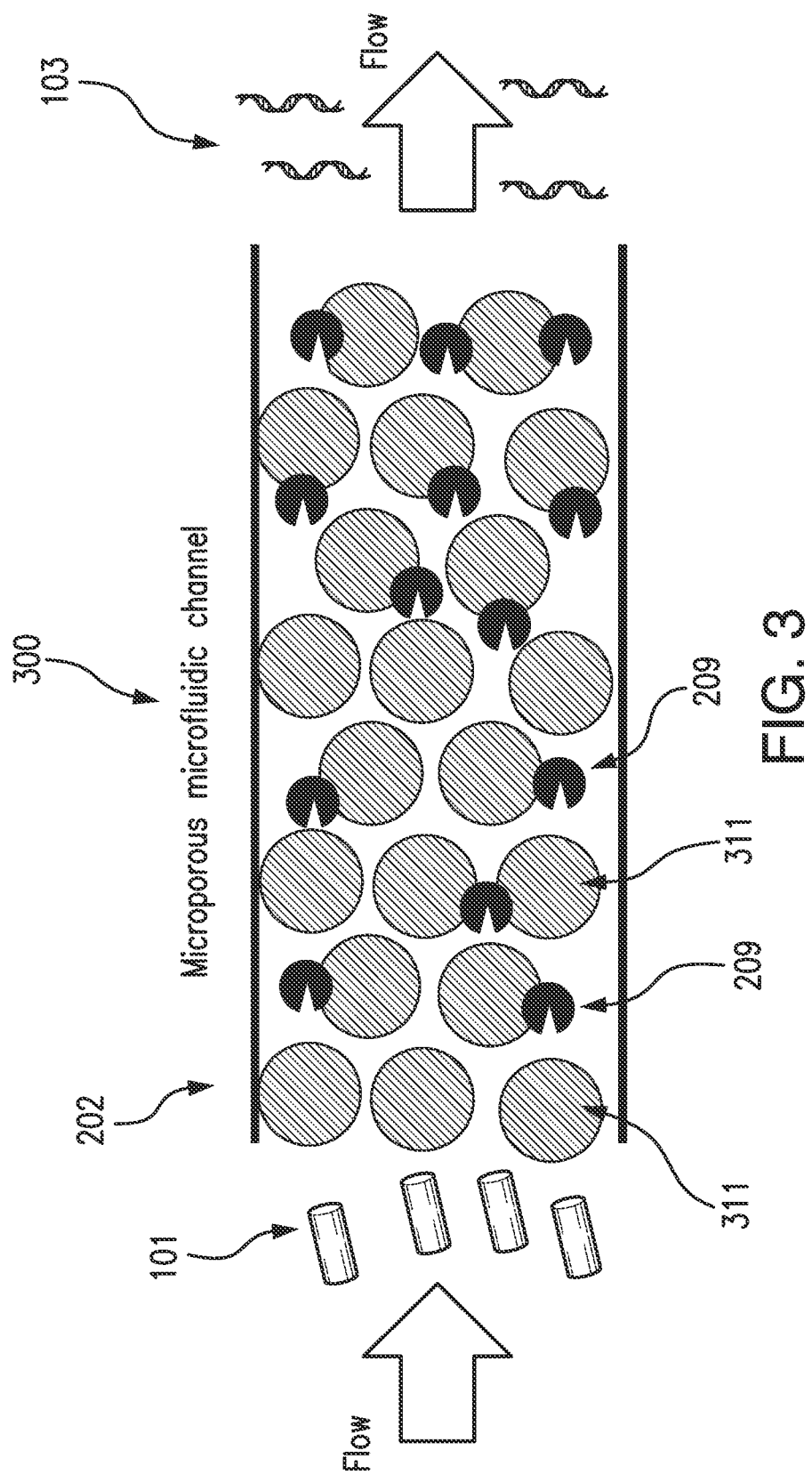
FIG. 3 shows a schematic illustration of a microfluidic device having a packed-column-of-beads microporous structure in accordance with an embodiment of the invention.

FIG. 3 shows a schematic illustration of a microfluidic device 300 having a microporous structure 311 comprising a packed-column-of-beads, in accordance with an embodiment of the invention. As illustrated in FIG. 3, microfluidic device 300 comprises a microfluidic channel 202 and a packed column of beads 311 located within the microfluidic channel 202. In one non-limiting embodiment, the beads may be chitosan beads. In some embodiments, the beads may also be chitosan-coated beads, such as, for example, chitosan-coated silica beads. The packed column of beads 311 are a microporous structure within the microfluidic channel 202. Microfluidic device 300 further comprises an enzyme 209 immobilized on the surface of the microporous column of beads 311. The immobilized enzyme 209 is configured to lyse pathogen cells in fluid flowing through the microfluidic channel 202. In one embodiment, the enzyme 209 is immobilized onto the beads before they are packed into the microfluidic channel 202. In one embodiment, the enzyme 209 is immobilized onto the beads via chitosan.

As pathogen cells 101 flow through microfluidic device 200 or microfluidic device 300, the cells will be in close proximity with the enzyme 209 due to the microporous nature of the channel, and thus the enzyme will interact with the cells 101. These interactions will cause the pathogen cells 101 to be lysed as they flow through. Having the enzyme 209 immobilized on the microporous structure 207 or 311 enables rapid continuous flow lysis as fluid containing pathogen cells 101 is pumped through the microfluidic device 200 or microfluidic device 300.

The microfluidic device 200 or microfluidic device 300 may further comprise additional regions or channels in fluid communication with channel 202. Such regions or channels may be used for downstream processing of the DNA 103 or other components 105 of the lysed pathogen cells 101, as known in the art. See, e.g., U.S. Pat. Nos. 7,629,124, 8,058,054 and 7,851,185, which are incorporated herein by reference in their entireties.

The immobilized enzyme 109 in microfluidic device 200 or microfluidic device 300 may be one or more proteolytic enzymes, such as, for example, lysozyme and/or proteinase K. The enzyme 109 may be covalently immobilized onto the surface of the microporous structure 207 of microfluidic device 200 or the microporous column of beads 311 of microfluidic device 300. The pathogen cells that microfluidic device 200 or microfluidic device 300 are configured to lyse may comprise bacteria cells (e.g. comprising gram-positive and gram-negative bacteria cells). The microfluidic device 200 or microfluidic device 300 may be configured to lyse cells in fluid flowing through the microfluidic channel 202. A suitable flow rate is selected to provide sufficient residence time in the microporous structure 207 to lyse the pathogen cells, as described herein.

The system includes one or more elements for controlling the flow rate of the continuously moving fluid in the channel(s), as well as system instruction or software for monitoring and controlling the flow rate in order to control the timing of each PCR cycle. The flow rate of the fluid through the microchannel is controlled by a pump mechanism. A pump mechanism can regulate the flow rate of the fluid by positive pressure at the upstream side or inlet of the microchannel, or by negative pressure at the downstream side or outlet of the microchannel.

Figure 4:
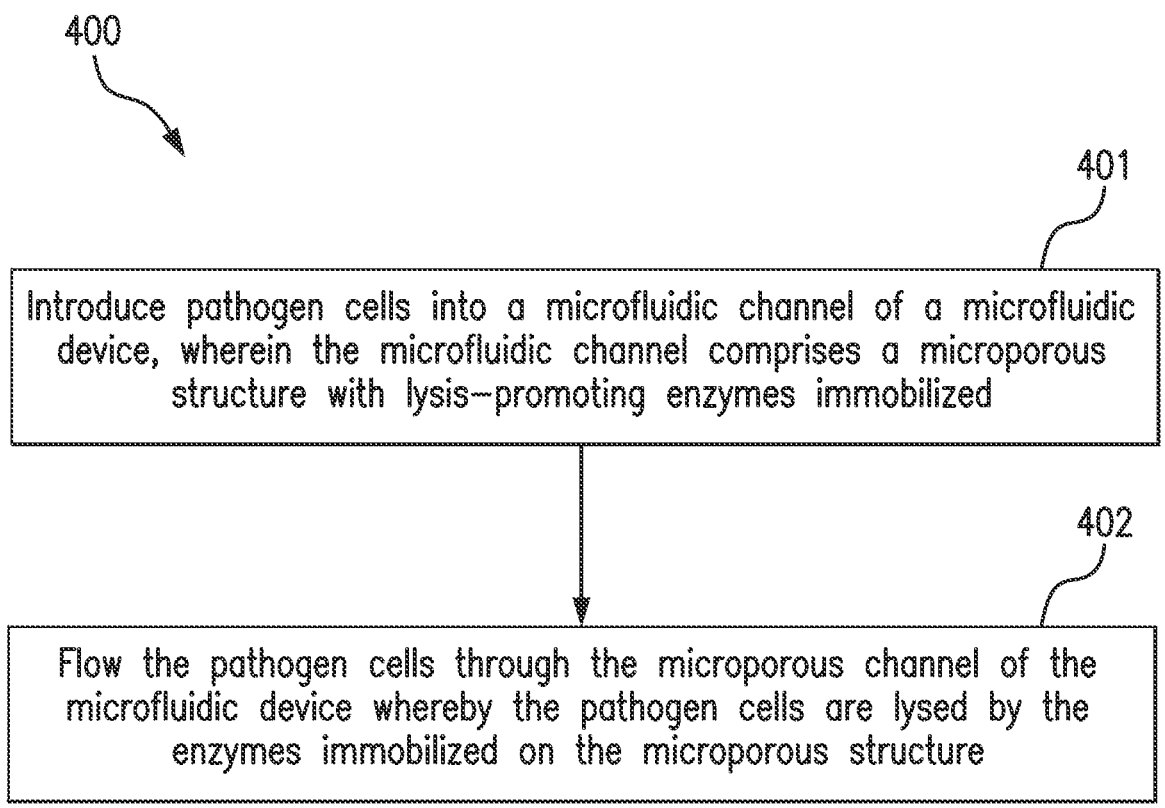
FIG. 4 is a flow chart illustrating a process for rapid continuous flow pathogen cell lysis according to an embodiment of the invention.

FIG. 4 shows a flow chart illustrating a process 400 for rapid continuous flow pathogen cell lysis according to an embodiment of the invention. Process 400 may begin in step 401, by introducing pathogen cells into a microfluidic channel of a microfluidic device, wherein the microfluidic channel comprises a microporous structure with lysis-promoting enzymes immobilized on a surface of the microporous structure. In step 402, the pathogen cells are made to flow through the microfluidic channel of the microfluidic device, resulting in the pathogen cells being lysed by the enzymes immobilized on the microporous structure. In some embodiments, the method further comprises providing the microfluidic device, wherein said microfluidic device comprises a microporous structure located in a microfluidic channel, and immobilizing a lysis-promoting enzyme on the surface of the microporous structure within the microfluidic device, before introducing pathogen cells into the microfluidic channel. In some embodiments, flowing the cells through the microfluidic channel may comprise pumping (e.g. with a syringe) or using negative pressure.

Figure 5:
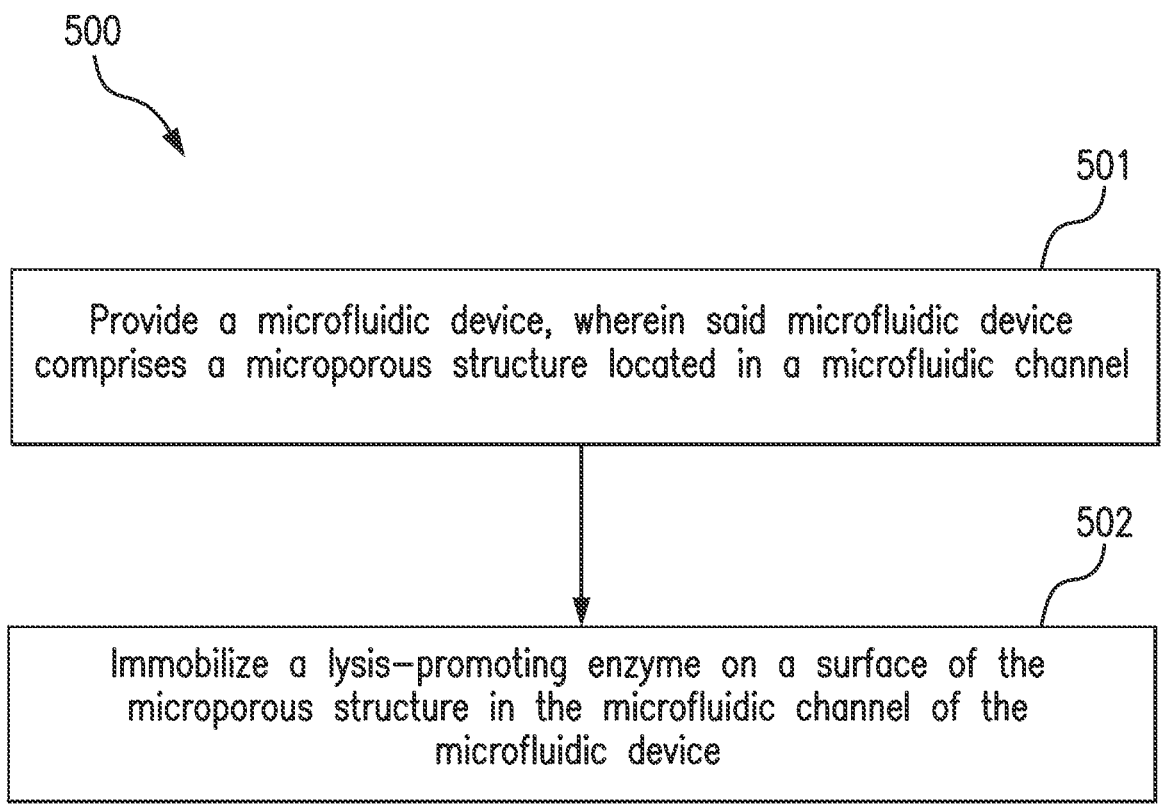
FIG. 5 is a flow chart illustrating a process for making a microfluidic device according to an embodiment of the invention.

FIG. 5 shows a flow chart illustrating a process 500 for making a microfluidic device according to an embodiment of the invention. Process 500 may begin in step 501, by providing a microfluidic device, wherein said microfluidic device comprises a microporous structure located in a microfluidic channel. In step 502, a lysis-promoting enzyme is immobilized on a surface of the microporous structure in the microfluidic channel of the microfluidic device.

In one non-limiting embodiment, microfluidic device 200 or microfluidic device 300 or process 400 may be used for the rapid processing of pathogen cells for the diagnosis of bloodstream or other infections.

While various embodiments of the present invention have been described above, it should be understood that they have been presented by way of example only, and not limitation. Thus, the breadth and scope of the present invention should not be limited by any of the above-described exemplary embodiments. Variations of the embodiments described above may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

What is claimed is:

1. A microfluidic device for rapid continuous flow pathogen cell lysis, the microfluidic device comprising:
    a microfluidic channel connected to a pump at the channel outlet;
    a microporous structure located and forming a pattern within the channel, the microporous structure comprising a surface, wherein the microporous structure is a monolith; and
    an enzyme immobilized on the surface of the microporous structure and configured to lyse pathogen cells in fluid continuously flowing through the microfluidic channel and the microporous structure, wherein the pump applies a negative pressure such that the fluid continuously flows through the microfluidic channel at a constant rate that provides sufficient residence time in the microporous structure to lyse the pathogen cells.

2. The device of claim 1, wherein the monolith is a polymer monolith.

3. The device of claim 1, wherein the monolith is a silica monolith.

4. The device of claim 1, wherein the microporous structure is a packed column of beads.

5. The device of claim 4, wherein the beads have bifunctional chemistry.

6. The device of claim 1, wherein the enzyme comprises one or more of lysozyme and/or proteinase K.

7. The device of claim 1, wherein the enzyme is covalently immobilized on the surface of the microporous structure.

8. The device of claim 1, wherein the pathogen cells are bacteria cells.

9. The device of claim 1, wherein the enzyme is configured to lyse pathogen cells in fluid flowing through the microfluidic channel.

10. The device of claim 1, additionally comprising at least one downstream channel in fluid communication with the microfluidic channel, wherein the at least one downstream channel separates DNA from other released components of the lysed pathogen cells.

* * * * *